United States Patent [19]

Coombs et al.

[11] Patent Number: 4,564,007
[45] Date of Patent: Jan. 14, 1986

[54] ORTHOPAEDIC EXTERNAL FIXATION DEVICES

[75] Inventors: Richard R. H. Coombs, Kingston; Mekki M. El-Saba, North Cheam, both of England

[73] Assignee: National Research Development Corp., London, England

[21] Appl. No.: 543,969

[22] Filed: Oct. 20, 1983

[30] Foreign Application Priority Data

Oct. 20, 1982 [GB] United Kingdom ............... 8229994

[51] Int. Cl.$^4$ ................................................ A61F 5/04
[52] U.S. Cl. .................................. 128/92 A; 128/92 B
[58] Field of Search ................ 128/92 A, 92 B, 92 R

[56] References Cited

U.S. PATENT DOCUMENTS

| | | | |
|---|---|---|---|
| 2,532,296 | 12/1950 | Giesen | 128/92 B |
| 3,741,205 | 6/1973 | Markolf et al. | 128/92 B |
| 3,877,424 | 4/1975 | Murray | 128/92 A |
| 4,059,102 | 11/1977 | Devas | 128/92 B |
| 4,175,555 | 11/1979 | Herbert | 128/92 B |
| 4,312,336 | 1/1982 | Danieletto et al. | 128/92 A |
| 4,463,753 | 8/1984 | Gustilo | 128/92 B |

Primary Examiner—Robert Peshock
Assistant Examiner—C. W. Shedd
Attorney, Agent, or Firm—Cushman, Darby & Cushman

[57] ABSTRACT

A device is proposed comprising a main support structure (10) and associated bone pins (32-36), each pin having leading and trailing treads (36, 34) of the same hand and pitch but with the latter thread of larger diameter to engage any one of a plurality of like threaded bores (19) through the main structure. Preferably the main structure includes an elongate frame (11) of closed loop form with a separable end (15) and two slide plates (12) mounted therein in adjustable end-to-end relation, each plate having at least two bores in an overall array orthogonal of the plates and longitudinal of the frame. The device also preferably has a cap (37) to cover the exposed trailing ends of the pins. The device is particularly useful in dorsal application for finger bone fracture fixation.

9 Claims, 8 Drawing Figures

U.S. Patent   Jan. 14, 1986   Sheet 1 of 2   4,564,007
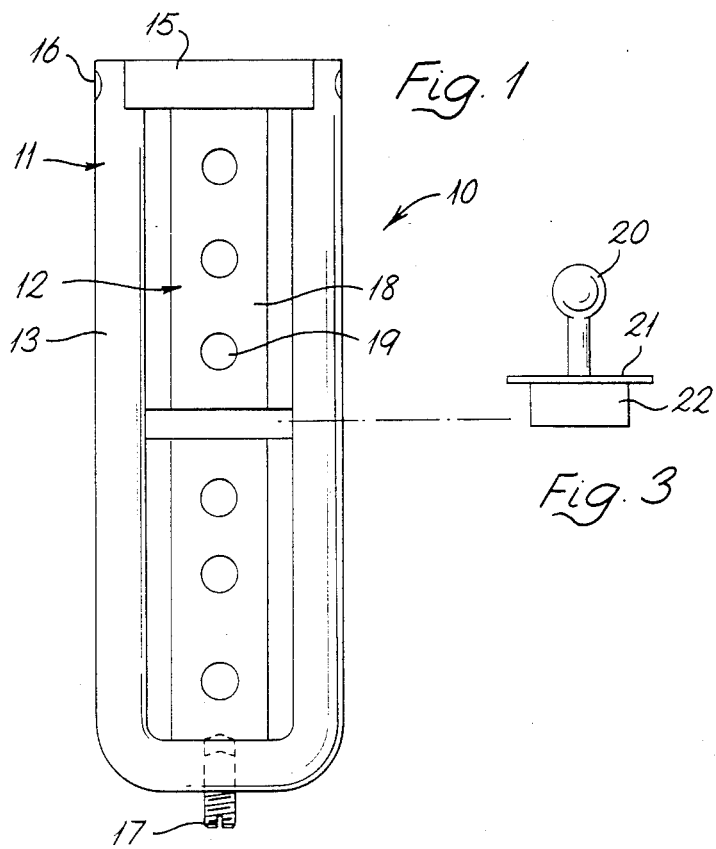
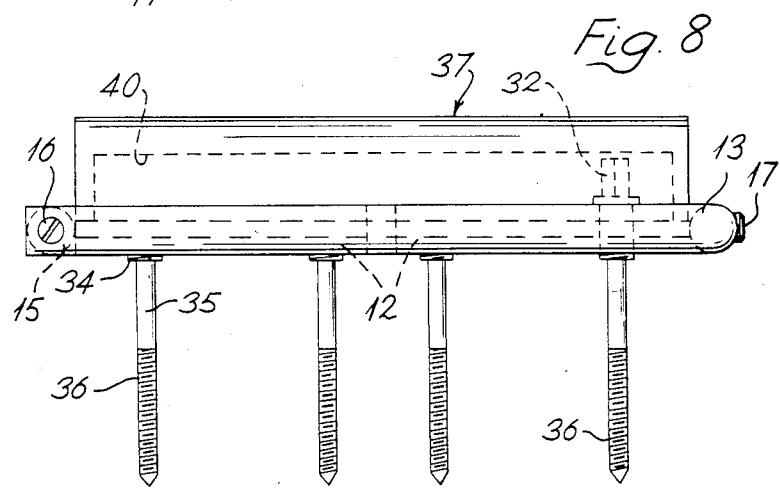

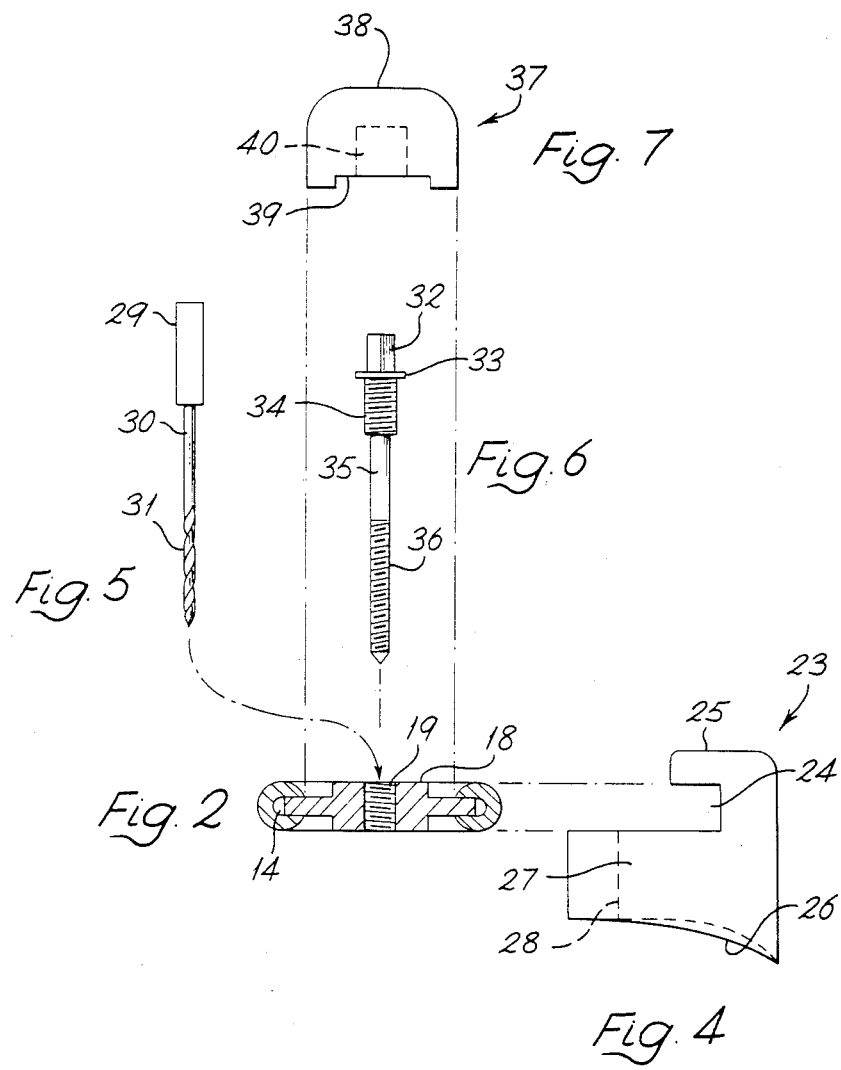

ORTHOPAEDIC EXTERNAL FIXATION DEVICES

This invention concerns orthopaedic external fixation devices of the kind involving components which are mutually interconnectable, usually in an adjustable manner, and connectable by way of bone pins to the fragments of a fractured bone, to form a support holding the bone fragments in a desired positional relationship while the fracture re-unites.

Devices of this kind offer significant advantages relative to traditional casts and the devices have accordingly found growing usage in recent years while, at the same time, numerous different designs have been proposed.

However, notwithstanding this activity, none of the available devices appears to be generally suited to use for commonly occurring fractures of the metacarpal and phalangeal bones of the hand.

The great majority of the existing devices are in fact intended for use for fractures in the principal long bones of the limbs and for other spacially extensive applications such that they are too large for use with the hand. Even so, the seemingly simple expedient of size reduction does not of itself render the existing devices suitable because, as is commonly the case in orthopaedics, different skeletal regions give rise to different individual treatment requirements.

In the case of the hand, any applied device should not immobilise the metacarpalphalangeal or interphalangeal joints for the period of time which is normal for fracture re-union, otherwise permanent immobility can result. Accordingly the device should be readily capable of production and effecting its intended function within a suitably compact size.

Moreover, mobility alone is not an ideal if the device is still such as to impair or hinder normal manual functions to a significant extent. The device should accordingly conform generally with the geometry of the related part of the hand.

Also, it is evident that the device should be simple to use even though of small size compared to prior forms.

Again, although not directly related to treatment, it is clearly desirable that the device should not be of such a form in relation to its size as to render it costly in manufacture.

Given this background, the present invention provides an orthopaedic external fixation device comprising a main support structure having a plurality of like threaded bores therethrough, and a plurality of similar bone pins, each said pin having spaced leading and trailing threaded portions of the same hand and pitch, but with the latter portion being of larger diameter and threadably engageable with any one of said bores.

In a form of such a device presently preferred for metacarpal and phalangeal fracture fixation the main support structure comprises an elongate apertured frame, two slide members longitudinally movably mounted in mutual end-to-end relation within said frame, and means for urging said slide members towards mutual inter-engagement, said bores each being formed in said slide members in an array disposed generally longitudinally of said frame, and said bores being directed generally orthogonally of said frame and slide members.

In this last form of device the frame is preferably of closed loop form, suitably generally rectangular in plan view, but with part thereof, such as one rectangular end, separable to allow release of the slide members.

The slide members are suitably of like plate form and each have at least two of said bores. The means for urging the slide members together is preferably adjustable, such as formed by a screw acting through the frame on one of the members.

The device also preferably includes a capping member to engage over the slide members and the exposed pin ends projecting therefrom following application of the device.

In its application to a fracture, the device is preferably associated with a stabilising member formed to engage separately the main support structure and the relevant part of the body to effect a predetermined spaced positional relationship therebetween. For the preferred form, this stabilising member is suitably in the general form of a bar having an axial slot adjacent one long face to receive one side of the frame, and having its opposite long face concavely transversely profiled to seat dorsally on the hand alongside a metacarpal or phalangeal bone.

Also, the preferred form of device is preferably applied in association with a spacer member engageable between the slide members to maintain the latter fully mutually separated whilst the bone pins are engaged, whereafter the spacer member is removed and the adjustment screw operated to close the slide members to effect compression across the fracture.

A fuller understanding of the invention may be gained from the following description of one embodiment of a preferred form of the invention, which description is given by way of example and with reference to the accompanying drawings, in which:

FIGS. 1 and 2 are respective plan and cross-sectional views of the main support structure of the embodiment;

FIG. 3 illustrates in perspective view an associated spacer member;

FIG. 4 illustrates in end view an associated stabilising member;

FIG. 5 illustrates in side view an associated drill bit;

FIG. 6 illustrates in side view an associated bone pin;

FIG. 7 illustrates in end view an associated capping member; and

FIG. 8 illustrates in side view the structure, pins and capping member of FIGS. 1, 6 and 7 in assembly.

The main support structure of FIGS. 1 and 2 is denoted generally at 10 and comprises an apertured frame 11 within which two like slide members 12 are movably mounted in end-to-end relation.

The frame 11 is of generally flat rectangular form made up from two parts of tubular metal. One part, 13, is of general U-shape of which the arms serve as the major rectangular sides, these arms each being provided with a longitudinal slot 14 wholly along its innermost surface area relative to the rectangular shape. The other part, 15, is straight and serves as the remaining end of the rectangular shape where it is separably secured by two screws 16 which pass through diametral bores in the free ends of the arms of part 13 into threaded engagement within the hollow of part 15. The base of part 13 is also diametrally bored and threaded at the midpoint therealong to receive screw 17 disposed in the plane of the rectangle.

The slide members 12 are each in the form of a plate having a width and thickness which allow sliding receipt in the open end of part 13, the length being just less than half of that of the frame aperture to allow a small extent of sliding movement for the members when captured in the frame by the part 15. A central portion 18 of each slide member is uniformly thickened over its length to equal the diameter of the frame material and this portion is formed with at least two like internally threaded bores 19 each extending orthogonally to the plane of the member and forming a longitudinal array in the frame.

The spacer member of FIG. 3 is of one-piece plastics material construction including a handle 20 leading at one end through a collar 21 to a blade 22, the blade being no thicker than the maximum extent of movement for the slide members in the frame.

The stabiliser member of FIG. 4 is also of one-piece plastics material construction in the general form of a bar 23 of the same or similar length to the frame 10, which bar is transversely slotted at 24 wholly along the length of one face nearer to one of the two adjacent faces, has the resultant arm 25 including the one adjacent face reduced in depth along its length, and has the other adjacent face formed to an assymmetrical concave transverse profile 26. The slot 24 is of a width corresponding to the diameter of the frame material, the shallower arm 25 bordering this slot is of a depth similar to the slot width, and the deeper arm 27 bordering the slot is of a depth no greater than that from the longer frame side to the nearer periphery of the bores 19.

In an alternative form, the arm 27 may be deeper but have its outer edge formed with a recess 28 along the major part of its length between its ends, as additionally shown in FIG. 4.

The drill bit of FIG. 5 has a trailing end shaft portion 29 leading, through an intermediate shaft portion 30 of reduced diameter, to a leading end, fluted cutting portion 31 of like reduced diameter.

The bone pin of FIG. 6 has a head 32 of square cross section leading through a collar 33 to a first threaded portion 34, then a shank portion 35 of reduced diameter, and finally a leading end threaded portion 36. The threaded portion 34 is engageable with any of the bores 19, it is shorter than the threaded portion 36, and the threads of these portions are of a common hand and pitch. The shank portion 35 has a length similar to the depth of the stabiliser member arm 27.

The capping member of FIG. 7 is of one-piece plastics material construction to seat within the frame aperture over the slide members and pin heads following assembly and application as will be appreciated hereinafter. This member is in the form of a slab 37 which is rounded over one major surface 38, and has its other major surface longitudinally recessed at 39 over a central portion thereof in complementary manner to the thickening of the slide members. Spaced within the borders of this recess is a longitudinal groove 40 having a length greater than the maximum distance between the two endmost bores 19 of the slide members when mounted in the frame, and transverse dimensions greater than those of the bone pin head 32.

In use of these illustrated components the fractured metacarpal or phalangeal bone to be supported is first manipulated to a desired positional relationship for reunion. The frame and slide members are assembled as in FIGS. 1 and 2, the screw 17 retracted to allow maximal separation of the slide members, the spacer member blade is located between the slide members, and the screw then tightened to secure the blade between the slide members. This assembly is then engaged in the stabilising member by location of one side of the frame in the slot 24, with the spacer member handle directed upwardly relative to FIG. 4. The profile 26 of the stabilising member allows this member to be seated, and readily held with adequate stability for the subsequent purposes, alongside the tissue around the relevant bone to position the frame/slide assembly in a generally predetermined, dorsally spaced position over the bone. The tissue is then marked through two bores 19 of each slide member, and the located assembly temporarily removed to allow small incisions to be made at each mark. The assembly is then repositioned and the drill bit used, in association with the bores as guides, to drill holes into the upper cortex of the underlying bone through each incision. It will be noted that the drill shaft is stepped to form a depth stop for this operation, the stop position being suitably related to the thickness of the stabiliser member arm 27. Individual bone pins are then applied to the drilled bone through the bores and, as the leading end threaded portions progress beyond the upper cortex, the trailing end threaded portions engage with the bores, the lengths of the threaded portions, their spacing, and the thickness of the stabilising member arm 27 being suitably related to this end. Also, relevant to this end is the use of a common hand and pitch for the threaded portions. Following this securement of the pins, the spacer member is removed, the screw 17 tightened to put the supported fracture under compression, the capping member is located over the pin heads, and the stabiliser member is removed.

The resultant assembly is shown by FIG. 8.

One benefit of the resultant assembly is that it is necessarily transversely compacted within the confines of the frame, without numerous irregular projections, so that joint mobility is ensured by appropriate dimensioning of the frame. Also, the assembly is readily compacted in its other dimension by virture of the direct interconnection of the pins with the slide members. This together with the generally flattened form of the assembly, its smoothness when capped, and its dorsal location, minimises interference with normal manual function. In addition, the range and form of the components, and their mode of interconnection, leads to simplicity in manufacture and usage bearing in mind the small scale of hand devices and surgery. It will also be appreciated that the assembly can be disassembled for cleaning.

While the invention has been described with more particular reference to the illustrated embodiment it is open to variation within the broader terms of the earlier description.

Such variation can be a matter of minor detail. For example, the invention has been developed primarily for use in association with the metacarpal and proximal phalangeal bones for which purpose two or three sizes of frame and slide members may be adequate, the larger of the latter having three bores each and the smaller having two each. Also, two different profiles may be appropriate for alternative metacarpal and phalangeal spacer members as respectively shown by solid and broken lines in FIG. 4. Again, the provision of a recess 28 may be appropriate in the stabilising member for smaller devices to ensure adequate support for the frame while allowing access for the drill bit and pins.

However, more significant variation can be effected, particularly if the compaction of the pin-support connection is applied to other larger long bones for external fixation.

We claim:

1. An orthopaedic external fixation device comprising:

a main support structure having a plurality of like threaded bores therethrough and a plurality of similar bone pins, each said pin having spaced leading and trailing threaded portions of the same hand and pitch, but with the latter portion being of larger diameter and threadably engageable with any one of said bores, said main support structure comprising an elongate apertured frame, two slide members movably mounted in mutual end-to-end relation within said frame, and means for urging said slide members towards interengagement, said bores being formed in said slide members in an array disposed generally longitudinally of said frame, and p0 said bores each being directed generally orthogonally of said frame and slide members.

2. A device according to claim 1 wherein said frame is of a closed loop form, but with part thereof separable to allow release of, said slide members.

3. A device according to claim 2 wherein said closed loop form is generally rectangular in plan view and said part includes one rectangular end.

4. A device according to claim 1 wherein said slide members are of like plate form and each have at least two of said bores.

5. A device according to claim 1 wherein said urging means comprises a screw acting through said frame on one of said slide members.

6. A device according to claim 1 comprising a capping member to engage over said slide members and the trailing end portions of said pins when connected therewith.

7. A device according to claim 1 in combination with a stabilising member formed to engage separately, to effect a predetermined spaced positional relationship therebetween, said main support structure and the part of a patient's body to which said device is to be applied.

8. A combination according to claim 7 wherein said stabilising member is in the general form of a bar having an axial slot adjacent one long face thereof to receive one side of said frame, and having its opposite long face concavely transversely profile to seat dorsally on a hand alongside a finger bone.

9. A device according to claim 1 in combination with a spacer member engageable between said slide members to maintain the latter fully mutually separated during application of said device.

* * * * *